United States Patent [19]

Kraskin

[11] 4,356,190

[45] * Oct. 26, 1982

[54] INHIBITING PRODUCTION OF UNDESIRABLE PRODUCTS ON BODY SURFACES AND ENVIRONS EMPLOYING AMINOPOLYCARBOXYLIC COMPOUNDS

[75] Inventor: Kenneth S. Kraskin, East Brunswick, N.J.

[73] Assignee: Personal Products Company, Milltown, N.J.

[*] Notice: The portion of the term of this patent subsequent to Jun. 16, 1998, has been disclaimed.

[21] Appl. No.: 351,919

[22] Filed: Oct. 16, 1978

Related U.S. Application Data

[63] Continuation-in-part of Ser. No. 803,706, Jun. 6, 1977, abandoned, which is a continuation-in-part of Ser. No. 574,488, May 5, 1975, abandoned, which is a continuation-in-part of Ser. No. 478,622, Jun. 2, 1974, Pat. No. 3,920,020.

[51] Int. Cl.$^3$ ............................................. A61K 31/195
[52] U.S. Cl. ..................................................... 424/319
[58] Field of Search ......................................... 424/319

[56] References Cited

U.S. PATENT DOCUMENTS 2,698,819  1/1955  Ziemlak .............................. 424/317
3,052,604  9/1962  Davis et al. ......................... 424/341
3,591,679  7/1971  Voss ................................... 424/127

OTHER PUBLICATIONS

Kirk et al., Encyclopedia of Chemical Technology, vol. 12 (1954), pp. 179–181.

*Primary Examiner*—Allen J. Robinson
*Attorney, Agent, or Firm*—Jason Lipow

[57] ABSTRACT

Methods, compositions and products are described which inhibit formation of undesirable products on body surfaces and environs resulting from microbial action on lipoidal materials in body secretions. Amino acid compounds are employed.

29 Claims, No Drawings

INHIBITING PRODUCTION OF UNDESIRABLE PRODUCTS ON BODY SURFACES AND ENVIRONS EMPLOYING AMINOPOLYCARBOXYLIC COMPOUNDS

DESCRIPTION OF THE INVENTION

This is a continuation-in-part of copending application Ser. No. 803,706, now abondoned, which was a continuation-in-part of Ser. No. 574,488 filed May 5, 1975 and now abandoned which was a continuation-in-part of Ser. No. 478,622 filed June 2, 1974 and issued as U.S. Pat. No. 3,920,020.

The present invention is directed to methods and means for controlling undesirable problems arising from microbial action on body fluids secreted or discharged from the body.

One of the long existing problems has been the unpleasant odors of menstrual fluid. Menstrual fluid contains a variety of substances including proteins and lipids. Normally, present in menstrual fluid are a wide number of gram negative and gram positive organisms which may act on these natural products. Bacterial action on proteins has been recognized as a source of amine malodor. Bacterial action on lipids could give rise to malodorous materials which are fatty acids.

Axillary malodor also has been a long existing problem. Axillary sweat is composed of secretions of both eccrine and apocrine sweat glands which are present in the axillary area. While eccrine sweat consists largely of water and salt, apocrine sweat is composed of a variety of substances including protein, carbohydrates and lipids. Numerous microorganisms including Staphylococci and Corynebacteria are present on the dermal surfaces of the axillary region. Microbial decomposition of lipids in apocrine sweat which results in production of lower fatty acids has been established as a primary cause of unpleasant odors in the axillary region. (Borick et al, *Antimicrobial Agents Annual*—1960, pp. 647-651, Plenum Press, Inc., New York)

Another problem, seemingly unrelated, is inflammatory skin disorders such as acne. Sebum is a lipid mixture secreted by the sebaceous glands and having a variety of fatty acids (Baughton et al, J. Invest, Dermat, 33, 49-55, 1959). Free fatty acids which have their source in the lipids are believed to be primarily responsible for the inflammatory disorder of the skin known as acne vulgaris (Freinkel et al, New Eng. J. Med 273, 850-854, 1965). Microorganisms, especially Corynebacterium acne, an organism present in both normal and diseased follicles, are reported to cause the formation of fatty acids (Scheimann et al, J. Invest, Dermat. 34, 171-174, 1960).

Germicides and antibiotics have been employed for the control of unpleasant odors of body products such as perspiration and menstrual fluid and for the alleviation of undesirable disorders such as acne. Thus, hexachlorophene, at one time was a popular constituent of preparations for controlling perspiration odors and antibiotics such as tetracycline have been successfully employed in the treatment of acne. However, germicides and antibiotics have accomplished these results by kill of the organisms, thereby disturbing the normal microbial balance. As is well-known, the kill of non-pathogenic organisms invites invasion by opportunist organisms such as pathogenic bacteria, yeast or fungi, whose presence may become manifest in febrile, inflammatory, dermatitic or other undesirable response. Thus, it is desirable that the control of unpleasant body odors or of disorders such as acne arising from microbial action on lipids be accomplished without significant kill of non-pathogenic microbial flora. It is further desirable that the results be accomplished without having adverse effects on human subjects.

Other methods for the control of the undesirable problems have been by the use of products which act on the causative agent after its formation. This approach is generally unsatisfactory tending to require employing relatively large amounts of treating agent and/or over an extended period. Moreover, the results have not been always completely satisfactory both in terms of completeness of control and in terms of avoidance of side reactions. It is highly desirable to control the undesirable problems by preventing the formation of the causative agent of these problems.

The present invention is based on the discovery that the foregoing problems as well as a number of other undesirable effects, may be attributed to microorganisms acting in a similar fashion and therefore, that the various problems may be controlled in a similar manner. It has further been discovered that this control may be brought about without significant kill of most bacterial flora.

It has been discovered according to the present invention that many of the undesirable problems such as menstrual malodor, axillary malodor and inflammatory disorders such as acne, caused by formation of undesirable products on body surfaces and environs as a result of microbial action on lipoidal materials in body secretions may be alleviated by inhibiting the formation of the undesirable products by applying to the situs of formation of the undesirable products, an inhibitory amount of an amino acid compound.

By "lipoidal materials in body secretion" is meant lipids (as understood in chemical terminology) which are present in body fluids which are secreted, excreted, discharged or exuded. Thus, "secretions" as herein employed include waste fluids. Typical secretions are sebum, perspiration, menstrual fluid, etc.

Lipids of importance in the present context are not only triglycerides but also phospholipids. The triglycerides may be represented by Formula I:

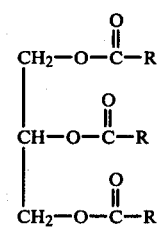

wherein in this and succeeding formulas, each R is a hydrocarbon radical derived from fatty acids and may be same or different. The phospholipids of primary concern in the present context are phosphotriglycerides which may be represented by the formula:

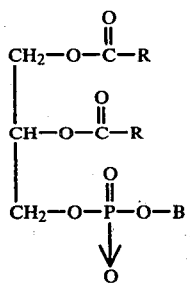

wherein R is as previously defined and B is a residue of an alcohol-amine compound such as an amino alcohol, a hydroxyquaternary ammonium base or a hydroxyamino acid.

The products which are formed or may be formed by microbial action on lipoidal materials are similar to those which may be formed on chemical hydrolysis. Thus, fatty acids and glycerol are produced from the triglycerides of Formula I as follows:

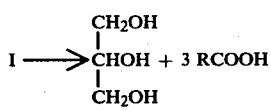

Since each R may be different, various fatty acids may be formed. Among the acids which may be formed are malodorous lower fatty acids such as butyric, isobutyric, isovaleric, etc. which are problems in axillary and menstrual malodor. These and other fatty acids including higher fatty acids (to $C_{18}$) may be sources of other undesirable problems such as inflammatory disorders of the skin.

Fatty acids may also arise from the phospholipids of Formula II:

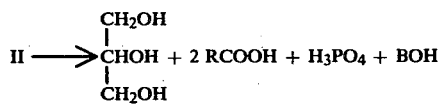

In preliminary experiments hereinafter described, phospholipids as a source of malodorous fatty acids was established.

It is further recognized that the undesirable fatty acids may arise in other ways as a result of microbial action and control of such fatty acids are intended to be embraced. However, the foregoing is believed to be a major source of fatty acids.

The expression "situs of formation" refers to the loci where the lipoidal secretions are retained or received and subject to microbial attack.

Normally, the "situs of formation" of primary concern are body or dermal surfaces and environs. These include skin, vagina and materials in close proximity to body surfaces such as catamenial devices, clothing, bed pads, etc. which are intended to receive or do receive the body fluids.

Amino acid compounds useful for the practice of the present invention generally have in the structure at least one arrangement of the amino group to acid group as follows:

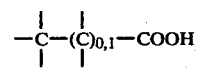

The acid group is preferably carboxylic, —COOH, but may be sulfonic, —SO$_2$OH, or phosphonic, —PO(OH)$_2$. The amino may be substituted and the carbon chain may contain groups such as hydroxyl —OH, sulfhydryl —SH, and ether —O—. Generally more than one acid containing group is present in the molecule and the acid containing group may be attached to the same amino nitrogen. The compounds may be termed "amino polyacid compounds."

An important group of compounds which inhibits the formation of fatty acids are the aminopolycarboxylic acid compounds. By "aminopolycarboxylic acid compound" is meant an amino acid or water-soluble salt thereof in which there is two or more substituent groups of the general structure:

$$-\underset{|}{\overset{|}{\text{C}}}-(\text{C})_{0,1}-\text{COOH}$$

in the molecule which are attached to one or more amino groups. Where there are more than two such substituent groups, the excess carboxyl groups may be esterified as long as at least two of the foregoing groups are present.

Preferred salts, especially for certain applications are monovalent salts such as sodium and potassium salts. For certain other applications, alkanolamine salts are preferred, especially di- and trialkanolamines such as triethanolamine, diethanolamine, triisopropanolamine, etc. The best known aminopolycarboxylic acid compounds are the acids and salts of ethylenediaminetetraacetic (EDTA) acid, diethylenetriaminepentaacetic (DTPA) acid and N-hydroxyethylethylenediaminetriaacetic (HEDTA) acid. These compounds are available commercially through trade names such as VERSEKE, VERSEHEX, VERSENOL, SEQUESTRENE, etc. Other typical compounds in this class include triethylenetetraaminehexaacetic acid, 1,2-diaminocyclohexane-N,N'-tetraacetic acid, N,N-dihydroxyethylethylenediaminediacetic acid, iminodiacetic acid, hydroxyethyliminodiacetic acid, and nitrilotriacetic acid and their salts as well as the propionic acid analogs.

The amino acid compounds are available as free acids, acid salts and salts. It is preferred that the form of the amino acid compound or combination thereof employed be such that at the situs of operation, the pH be near neutrality, about 6.2 to about 8.5. However, useful results may be obtained if the pH is at least as high as 4.0. Frequently, it is convenient to prepare the salt or acid salt by mixing the acid and base in the composition.

The amino acid compounds are useful in such amounts as would give a final concentration of at least 0.01% by weight of the body secretion. The upper limit is dictated primarily by practical considerations. Generally speaking, not much advantage is gained by adding an amount which would give a concentration greater than about 0.5% by weight of body secretion. The preferred amounts depend on the purpose, place and method of application and on the particular compound. Thus, where microbial population is expected to be high, such as in menstrual fluid, larger amounts preferably are employed. Thus, for control of menstrual malodor, at least about 0.04% by weight of menstrual fluid is desirable and 0.10% or more is preferred. Within the broad scope, preferred ranges are hereinafter disclosed in the context of the particular use and method of application.

The amino acid compound may be applied to the situs of formation of microbially produced undesirable products in various ways. In its use for the inhibition of formation of malodorous materials in menstrual fluid, the amino acid compound is conveniently applied to receptacles for the fluid such as catamenial dressings or to such other materials which may receive the fluid such as bed pads, clothing, etc. By "catamenial dressings" is meant sanitary napkins, tampons and interlabial pads which usually consist of a core of one or more layers of highly absorbent, relatively dense materials which have a fluid permeable, soft, knitted, woven or non-woven wrapper. The cores are conventionally made of layers of fibers such as carded cotton webs, air-layered cellulosic fiber webs, comminuted wood pulp bats, tissue pulp or like materials but may be made of newer synthetic materials such as synthetic polymer foams and fibers. Although the amino acid compound may be distributed uniformly through the catamenial dressing, it is more useful to place it in that portion which first contacts the body discharge. Thus, it is preferably applied to the surface of the absorbent cores of the dressings or to the covers or both in such a manner that the amino acid compound is present on the surfaces thereof in an amount ranging from about 0.001 g. per square inch to about 0.1 g. per square inch. Such amounts have been found to provide the desired concentration in terms of the amount of amino acid compound to total body secretion. A preferred range for catamenial dressings is from about 0.004 to 0.06 g. per square inch.

The amino acid compounds may be applied to the catamenial dressings during manufacture or use. When applied during manufacture, it may be applied by spraying either an aqueous spray or an aerosol spray, padding, soaking, or by dusting or any known method for applying materials thereto. An aerosol spray may employ such propellants as dichlorodifluoromethane, trichlorofluoromethane; a solvent spray may employ substantially inert solvents such as isopropanol. The use of a propellant or inert organic solvent is preferred over an aqueous solution or suspension to minimize drying of the catamenial dressing subsequent to the application of the amino acid compound. In addition, the amino acid compound may be applied to the dressing prior to use in dry powder formulations.

The application of the amino acid compound may be made topically to the dermal surfaces preferably in a suitable carrier such that it is distributed on the dermal surfaces in amounts sufficient to provide at least 0.01% by weight of body secretion as hereinbefore specified. The application preferably is made prior to the secretion of the body fluid to preclude substantially completely the formation of the undesirable products. However, application may be made subsequent thereto by minimizing microbial action on the body secretions. Topical applications to dermal surfaces are suitable both for inhibiting the development of undesirable inflammatory conditions of the skin and for inhibiting malodor development. When the application is to be topical, the carrier may be in solid, liquid, spray or semi-solid form in cosmetic or pharmaceutical carriers intended for topical use. Carriers into which the amino acid compound may be incorporated include lotions, ointments, aerosols, water solutions, creams, pulverized mixtures, gel sticks and the like. The various additives and diluents include ointment additives such as polysorbate 80, polyoxyethylene sorbitan trioleate; surfactants and emulsifiers such as lauryl sulfate, sodium cetyl sulfate, glyceryl monostearate, diethylaminoethyl alkyl amide phosphate, isopropyl myristate, octyl alcohol, glyceryl and glycol esters of stearic acids; glycols such as propylene glycol; other polyhydroxy compounds such as glycerol, sorbitol; alcohols such as ethanol, isopropanol; witch hazel (Hamamelis water); perfumes; essential oils; propellants such as halogenated hydrocarbons, e.g., dichlorodifluoromethane, trichlorofluoroethane, etc., carbon dioxide and nitrogen; solid diluents such as calcium carbonate, starch, bentonite, talc; and silicone-type fluids such as polysiloxane fluid. Selection of the particular carrier varies with use. In dermal preparations for the control of inflammatory skin conditions, aqueous compositions are desirable. Preferred compositions for such applications are those comprising witch hazel as a carrier component.

In compositions for topical application, the amino acid compound is employed in an amount of at least 0.05% by weight. This is desirable in view of the diluting and possible partial deactivating effect of the carrier. The amino acid compound may be present in larger amounts and may even constitute the major portion of the composition although less desirable from practical considerations. For topical application, the amino acid compounds are preferably employed in the form of alkanolamine salts. When the carrier is aqueous, the salt may be formed in the composition by admixing the free acid and the alkanolamine in the aqueous carrier.

In preparations for the control of inflammatory skin conditions, the amino acid compounds employed are preferably in the form of acid or water soluble monovalent salt or mixtures thereof in an aqueous composition in an amount of from about 2 to about 15% by weight when based on the weight of free acid.

When incorporating the amino acid compound into a lotion, cream or aerosol, the amino acid compound may be added in a solvent compatible with the system in which it is incorporated such as water, glycerol, propylene glycol, tripropylene glycol, methyl ether, ethanol, etc. Alternatively, the amino acid compound may be added to the final composition and intimately admixed therewith. Such would be the preferred method for preparing dusting powders as well as aqueous solutions such as in witch hazel.

The compositions above described are applied to the situs of production of undesirable materials by the various microorganisms. The microorganisms associated with the production of materials contributing to menstrual malodor include Gram Negative organisms such as *Proteus mirabilis, Klebsiella pneumoniae, Aerobacter aerogenes, Escherichia coli, Pseudomonas aeruginosa*, etc., Gram Positive organisms such as *Staphylococcus aureus, Streptococcus faecalis*, etc. and yeast such as *Candida Albicans*, etc. The microorganisms associated with the production of substances contributing to axillary malodor are those normally present on the skin surfaces of which those of the genera Corynebacterium and Staphylococcus are the most important. Corynebacteria are also associated with the production of acids contributing to the undersirable inflammatory conditions of the skin. By employing the compounds and compositions in accordance with the present invention, the action of the microorganisms which results in the production of undesirable acids is somehow inhibited or altered. The amino acid compound is believed to be proceeding by removal of the necessary metallic co-factor for the enzymatic production of fatty acids. However, the invention is not limited to any particular theory and the preventative control of fatty acid production may be achieved without necessarily causing detrimental effect on microbial flora.

The effectiveness of the amino acid compound in inhibiting the formation of undesirable fatty acids from lipids was determined by gas chromatographic analyses and the effectiveness in odor control was determined by organoleptic techniques.

Gas chromatographic analyses employed comparisons with known acids. The method employed was as follows: Fatty acids extracted in diethyl ether from acidified test samples were determined by gas chromatographic procedures using a Hewlett-Packard 7620A instrument and Porapak QA 80/100 mesh in a 6 ft.×2 mm. I.D. glass column. The instrument was programmed at 135° C. @40° C. per minute, holding the upper limits for six minutes. Helium was used as a carrier gas at a pressure of 60 PSI and a flow rate of 40 ml./min.

For evaluation of the effectiveness of catamenial dressings in odor control, quantitative organoleptic evaluation method was employed referred to as the Modified Ratio Scale Organoleptic Evaluation method as follows.

The Modified Ratio Scale Organoleptic Evaluation Method

This method is devised so that data obtained from an organoleptic appraisal panel may produce an evaluation of a sample characterized as an absolute value for odor intensity. Thus, not only can the difference between two samples of an odorant placed in different environments (e.g., on a pad with and without deodorizer) be detected, but further, the evaluation will indicate, quantitatively, as to whether the odor intensities of the samples are strong or weak. For example, one sample may contain a deodorizer which is many times as effective as that contained in a second sample. This notwithstanding, both deodorizers may only produce a small decrease in the odor intensity, all of which is indicated by the subject evaluation method.

The first step in this method is to determine the threshold concentration of the odorant. The method used is described by Fred H. Steiger in Chemical Technology, Volume 1, pg. 225, April 1971, wherein the determination of the odor threshold concentration for ethylamine is described, applying the Weibull distribution function. Generally, this procedure requires the gathering of organoleptic data from a panel presented with a series of samples containing odorant in increasing concentrations in order to determine the concentration level at which an arbitrary percentage of the panelists can detect the odor. For the purposes of the current evaluation that arbitrary percentage is chosen as the cumulative 50% level. As so determined, the threshold concentration of the odorant is specific to the odorant and the conditions of the sampling procedure.

The method employed herein for panel evaluation is to present each panelist with a series of samples, in a sampling apparatus which consists of an opaque, one pint, polyethylene Mason jar having a polyethylene screw cap fitted onto its neck. The jar is internally lined with a polyethylene bag and a Buchner funnel is fitted about the cap, with the narrow outlet portion of the funnel, below the filter plate of the funnel, extending through the cap and into the lined jar. A sample is placed in the jar, the jar is capped with the Buchner funnel fitted in place and a watch glass is placed across the wide inlet portion of the funnel. The sample is then allowed to equilibrate for one hour at ambient conditions. For the purpose of the threshold determination, the samples each comprise a specific concentration of the odorant in a water solution, a total of 3 ml. of solution being placed in the jar. A panel of about 30 women are presented with a series of equilibrated samples of increasing concentration and, starting with a sample at zero concentration (water only), are asked to report the first sample having a detectable odor. The panelists are instructed to sniff each sample in turn, pausing 30 seconds between samplings. The accumulated data is organized to establish the cumulative percentage of the panel which detects an odor at each concentration level corresponding to each sample. The data, so organized, is plotted as described in the aforementioned Steiger article on Weibull Probability Paper with the concentration as the abscissa and the cumulative percentage of the panel as the ordinate. The concentration at 50% is then taken as the threshold concentration.

Having established the threshold value, the Modified Ratio Scale Method is applied by preparing a master curve. Using the same testing apparatus, a series of samples are prepared and presented to the panel wherein the concentrations of odorant can be expressed as multiples of the threshold concentration or odor units. One of these samples is 20 times the threshold concentration (20 odor units).

In accordance with the standard method of Ratio Scaling, each panelist is asked to evaluate the set of samples before her and to assign a value to the odor intensity of each sample in proportion to the intensity of the other samples. The panelists are free to choose whatever scale they wish. For example, a panelist may assign 10 to the strongest sample. A sample having half that intensity, in accordance with this panelist's evaluation, would then be assigned a value of 5. The accumulated data then consists of a series of evaluations for each panelist, each series being based upon the individual panelists' scale. Arbitrarily, a ratio scale value of 100 is assigned to the sample concentration of 20 times threshold concentration. Each of the panelists' evaluations are then proportioned to bring their individual scales to the basis of 100 for 20 times threshold concentration. For example, the evaluations of a panelist assigning a value of 10 to a first sample having a concentration of 20 times threshold concentration will be proportioned to show, for that panelist, a value of 100 for the first sample and a value of 50 for the second sample. The data is now organized so that, for each sample corresponding to a specific multiple of the threshold concentration, there is a series of Ratio Values, all on the same scale (20 times Threshold Concentration=100) corresponding to each panelist's evaluation of this sample. The geometric means of the ratio values for each sample is calculated and that value is taken as the Ratio Value for that multiple of threshold concentration.

When the log of the Ratio Value is plotted, as the ordinate, against the log of the multiple of threshold concentration, a straight line, fitted to the data points between 3 to 20 times threshold concentration gives an excellent correlation.

It has been discovered that irrespective of which amine odorant is tested, when a threshold concentration is determined for that specific odorant and the method of constructing a Master Curve as described above is followed, the resulting Master Curves are superimposable between multiples of threshold concentration of about 3 to about 20.

The curve obtained in this way for isobutyric acid, a chemically dissimilar material also was superimposable on the Master Curves for the amines. Thus, the reference odorant in any test may be chemically dissimilar to the odor constituent or constituents being tested.

The Master Curve may now be used to evaluate the odor intensity of any odorant when placed in any environment such as, for example, on a pad of untreated cellulosic fibers or on a pad of fibers containing deodorizing material and, in addition to obtaining comparisons between the relative intensity of the samples tested, an absolute measure of the intensity of each sample may be obtained. To do this, the panel is presented with a series of samples, one of which is a standard sample consisting of known concentration of the odorant being tested in an environment identical to that used in producing the Master Curve. Preferably, this standard sample is chosen as having 20 times the threshold concentration and hence, a Ratio Value of 100 on the Master Curve.

The panelists are again asked to evaluate the series of samples using whatever scale they choose. Based on the value which each panelist gives to the intensity of the standard sample, all other values given by the panelists are proportioned so as to be consistent with the rating of the standard sample, e.g., a panelist assigning a value of 50 to the standard sample and 5 to a second sample of unknown intensity will have these values proportioned so the standard will be given a Ratio Value of 100 and the unknown sample given a Ratio Value of 10. By referring to the Master Curve, it can be determined that the panelists now proportioned Ratio Value of 10 for the second sample is equivalent to an odor intensity of a certain number of multiples of threshold concentration as read from the Master Curve were 1.2, the odor intensity of the sample of unknown intensity, in the test environment, is the same as a sample having an odorant concentration of 1.2 times the threshold concentration in the standard environment.

Preliminary determinations were made in connection with the menstrual malodor aspect of the present invention to establish the presence of phospholipids in menstrual fluid and to establish malodorous fatty acid production by microbial flora commonly present in menstrual fluid.

The presence of significant amounts of phospholipids in menstrual fluid was established by a procedure consisting of heating the phospholipids with perchloric acid to oxidize the organic portion of the molecule and convert the phosphorus to a blue phosphomolybdate which may be read colorimetrically as more fully described on pp. 375-376 of "Bray's Clinical Laboratory Methods" by Bauer et al, 17th Edition, C. W. Mosby Co., 1969. Ten samples of menstrual fluid were collected in cups and subjected to phospholipid analyses. The analyses established the presence of from 2250 to 4140 ppm of phospholipids amounting to from 0.225 to 0.4% of the fluid.

To establish the ability of microorganisms commonly present in menstrual fluid to produce malodorous fatty acids, separate samples of sterile human blood were inoculated with different organisms previously isolated from menstrual fluid, followed by incubation and analysis by gas chromatography as hereinafter described. In the determination, blood was employed instead of menstrual fluid because of the availability of sterile blood and the desirability of a sterile substrate to identify fatty acid production as being caused by the organism used in inoculation. The suitability of substituting blood was based on the known fact of the presence of triglycerides in both blood and menstrual fluid and on preliminary experiments on six samples each of human blood and menstrual fluid which showed average total phospholipids to be 2807 ppm and 2771 ppm respectively. The methods employed and the results obtained were as follows:

2.5 ml. test samples of sterile whole human blood were separately inoculated with a 0.2 ml. bacterial cell suspension of various test organisms previously isolated by conventional methods from menstrual fluid. The test samples as well as an uninoculated control sample were incubated at 37° C. for 24 hours in a constant temperature bath with constant shaking at 200 r.p.m. Thereafter, all samples were subjected to gas chromatographic analyses. The results are seen in Table A.

TABLE A

| | FATTY ACIDS PRESENT (ppm) | | |
|---|---|---|---|
| | Iso-butyric | Butyric | Iso-valeric |
| Uninoculated Control | 0 | 0 | 3.5 |
| Gram Negative Bacteria | | | |
| Proteus mirabilis | 59.5 | 9 | 111.7 |
| Klebsiella pneumoniae | 0 | 0 | 11.3 |
| Aerobacter aerogenes | 0 | 8.7 | 15.0 |
| Escherichia coli | 0 | 0 | 0 |
| Pseudomonas aeruginosa | 0 | 0 | 0 |
| Gram Positive Bacteria | | | |
| Staphylococcus aureus | 13.7 | 0 | 50.5 |
| Streptococcus faecalis | 0 | 0 | 39.1 |
| Yeast | | | |
| Candida albicans | 12 | 0 | 38.5 |

The following examples illustrate the various aspects of the present invention but are not to be construed as limiting:

EXAMPLE I

Two menstrual fluid samples were collected and analyses were made initially for fatty acids: isobutyric, butyric and isovaleric by gas chromatography on untreated, unincubated fluid. Thereafter, test samples of about 2 ml. of each menstrual fluid were prepared. Two sets, each set containing two different samples of menstrual fluid were treated as follows: to one set, disodium ethylenediaminetetraacetate was added to provide a final concentration thereof of 0.2% by weight of menstrual fluid and the other set was left untreated. Both treated and untreated samples were incubated at 37° C. for 24 hours and thereafter analyzed by gas chromatography for the fatty acids previously named. The results are seen in Table I.

TABLE I

| | | FATTY ACIDS (ppm) | | |
|---|---|---|---|---|
| | | Iso-butyric | Butyric | Isovaleric |
| Sample 1 | Freshly Obtained Unincubated, Untreated Control | 0 | 36 | 0 |
| | Incubated Untreated | 685.7 | 1014.0 | 857.1 |
| | Incubated Na₂EDTA Treated | 0 | 16.6 | 14.3 |
| Sample 2 | Freshly Obtained Unincubated Untreated Control | 0 | 0 | 0 |
| | Incubated Untreated | 475.0 | 307.0 | 336.0 |
| | Incubated Na₂EDTA Treated | 4.0 | 13.0 | 9.0 |

EXAMPLE II

Five samples of 2.5 ml. of sterile human blood were inoculated with 0.2 ml. of *Proteus mirabilis* suspension. To four of the samples, disodium ethylenediaminetetraacetate was added to supply amounts ranging from 0.04% to 0.2%. One sample was an inoculated control containing no EDTA compound. In addition, an uninoculated control sample was prepared of 2.5 ml. of the blood to which 0.2 ml. of sterile distilled water was added. The treated and untreated inoculated samples and an uninoculated control sample were then incubated for 24 hours at 37° C. in a constant temperature water bath with shaking at 200 r.p.m. At the end of this period aliquots were tested for the presence of the acids by gas chromatography. The results are given in Table II.

TABLE II

| TREATMENT | Fatty Acids (ppm) | |
|---|---|---|
| % Na₂EDTA | Isobutyric | Isovaleric |
| Proteus + No Na₂EDTA | 102.7 | 98.2 |
| Proteus + 0.04% Na₂EDTA | 28.4 | 52.3 |
| Proteus + 0.1% Na₂EDTA | 6.6 | 17.5 |
| Proteus + 0.2% Na₂EDTA | 7.9 | 17.6 |
| Untreated Sterile Blood | 0 | 0 |

EXAMPLE III

Sterile blood inoculated with *Proteus mirabilis* was placed on treated and untreated samples of fluff pads and sanitary napkins. To prepare treated samples, a 14 percent aqueous solution of a blend of disodium and tetrasodium ethylenediaminetetraacetate (pH 7) first was applied at various positions and concentrations to samples of fluff pads or samples of sanitary napkins by soaking, spraying or padding on the cover. The samples were thereafter dried and the amount of the ethylenediaminetetraacetate salts dispersed in the samples determined by weighing. Blood previously inoculated with *Proteus mirabilis* was added to the various treated samples as well as to an untreated sample and to a dimethylamine reference odorant sample. (Three milliliters were used for fluff pads and five milliliters were used for the sanitary napkins). The samples then were incubated at 37° C. for 24 hours and thereafter subjected to organoleptic testing in the manner previously described. The results showing significant odor reduction are seen in Table III.

TABLE III

| | Percent Odor Reduction[1] with Various Placements[4] of EDTA | | | | | |
|---|---|---|---|---|---|---|
| Conc. of EDTA[5] grams per gram of inoculum tested | I dispersed throughout fluff | II paper tissue as filter over fluff pad | III non-woven cover on sanitary napkin | IV cotton fabric as filter over fluff pad | V top fluff surface | VI embossed section of sanitary napkin |
| 0.0005[2] | —[3] | 46 | — | — | — | — |
| 0.0016 | — | — | 48 | — | — | — |
| 0.0050 | — | — | — | 52 | — | 24 |
| 0.0060 | — | — | — | — | 46 | — |
| 0.0084 | — | — | — | — | 50 | 42 |
| 0.0100 | — | — | — | — | — | 40 |
| 0.0140 | 68 | — | — | — | — | — |
| 0.0200 | — | — | — | — | — | 58 |
| 0.0330 | — | — | — | — | — | — |

[1] as compared with untreated control, in terms of perceived odor
[2] estimated from concentration of EDTA solution applied in spray during making of tissue
[3] Dashed lines (—) indicates not tested.
[4] Methods employed to disperse EDTA:
I. soaking in aqueous 14% solution,
II. aqueous spray,
III. padding (place in solution thereafter roller wring dry),
IV. padding,
V. aqueous spray,
VI. aqueous spray
[5] The neutral (pH7) solution of ethylenediaminetetraacetate was prepared by dissolving 10.0 grams of tetrasodium ethylenediaminetetraacetate and 11.4 grams of disodiumethylenediaminetetraacetate in 125 milliters of distilled water. The resulting solution is about a 14% (weight) solution.

EXAMPLE IV

In an experiment carried out over a period of six months, a panel of seven subjects wore sanitary napkins menstrually for a minimum of four hours or until the discharge of menstrual fluid was such that a change of napkin was necessary. Within thirty minutes after removal, the napkins were inspected and physical data such as weight, physical appearance and stain area were recorded. Thereafter, the napkins were incubated at 30° C. for one hour and thereafter evaluated for odor.

This procedure was repeated by each panelist with a treated and untreated (control) napkins but on alternate months. In some cases, the data was collected over the entire six-month period while in other cases, the data was only for two months or for four months. The selection of product to a given panelist was randomized so that factors such as climate or activity changes would have minimum influence.

The treated napkins employed had been prepared by removing the non-woven fabric cover of a MODESS* Sanitary Napkin, passing the absorbent tissue inner padding through a solution of a blend of disodium and tetrasodium ethylenediaminetetraacetate (prepared as described in Example III), drying and replacing in the fluid pervious cover. The concentration of the salt after drying was 0.004 gram per square inch of fabric.

*Trademark of JOHNSON & JOHNSON

The odor data from all subjects for this period were pooled and the odor intensity responses for test products compared with a control. The odor response for twenty-five treated and twenty-five untreated napkins were described in odor units of from zero to 21 (maximum). The untreated napkins had odor units ranging from 3 to 21 with five napkins above 15. Ten of the treated napkins had odor units of less than 3 and none above 11.

EXAMPLE V

Two milliliter portions of dilute human plasma (1 part of plasma to 2 parts of sterile distilled water) were inoculated with Corynebacterium. To three of the samples, disodium ethylenediaminetetraacetate was added to produce a concentration thereof of 0.1%, 0.2% and 0.5%. One sample containing no sodium ethylenediaminetetraacetate served as an untreated control. In addition, an uninoculated control sample of unmodified dilute human plasma was prepared. The test and control samples were incubated at 37° C. with shaking at approximately 200 r.p.m. for 24 hours. At the end of this period, the samples were tested for free fatty acids by gas chromatography. The results obtained were as follows:

TABLE IV

| Treatment | Fatty Acids (ppm) | |
| --- | --- | --- |
| | Isobutyric | Isovaleric |
| Untreated sterile plasma | 0 | 0 |
| Corynebacterium Inoculum – No Na$_2$EDTA | 155 | 564 |
| Corynebacterium Inoculum + 0.5% Na$_2$EDTA | 12 | 22 |
| Corynebacterium Inoculum + 0.2% Na$_2$EDTA | 25 | 49 |
| Corynebacterium Inoculum + 0.1% Na$_2$EDTA | 22 | 41 |

EXAMPLE VI

Disodium ethylenediaminetetraacetate was added to a two milliliter portion of a brain-heart-infusion (BHI) broth containing natural axillary flora consisting primarily of Corynebacterium and Staphylococcus to produce a final concentration of 0.5% by weight. A second two milliliter portion of inoculated broth contained no disodium ethylenediaminetetraacetate. In addition, a two milliliter portion of sterile BHI broth served as an uninoculated control. The test and control samples were incubated at 37° C. with shaking at 200 r.p.m. for 24 hours. At the end of this period, samples were determined for free fatty acids by gas chromatography. The results are seen in Table V.

TABLE V

| Treatment | Fatty Acids (ppm) | |
| --- | --- | --- |
| | Isobutyric | Isovaleric |
| Sterile BHI | 0 | 0 |
| BHI inoculated with underarm culture | 32 | 57 |
| BHI inoculated with underarm culture + 0.5% Na$_2$EDTA | 0 | 0 |

EXAMPLE VII

An aqueous solution containing 0.45 percent by weight of a mixture Na$_2$EDTA and Na$_4$EDTA (prepared as described in Ex. III) was applied to one axilla of a test subject by means of a sterile gauze pad which had been wetted with the solution. Sterile distilled water was applied in a similar manner to the other axilla and served as the untreated control. Both axilla were evaluated by olfactory sensing twice daily to determine compartive odor development and intensity. The treated axilla exhibited a substantial deodorant effect.

EXAMPLE VIII

A cream suitable for application to the body for inflammatory disorders of the skin is prepared by (1) heating Part A (below) to 70° (2) Part B (below) to 75° C. (3) adding Part B to Part A with agitation and (4) adjusting the pH to 5.5 with dilute sodium hydroxide.

| | % Weight |
| --- | --- |
| Part A | |
| Cetyl alcohol | 2.5 |
| Stearyl alcohol | 5.0 |
| Isopropyl myristate | 2.0 |
| Light silicone oil | 1.0 |
| "Emplex"[1] | 1.5 |
| Methyl paraben[2] | 0.15 |
| Propyl paraben[3] | 0.05 |
| Part B | |
| Deionized water | 78.8 |
| Disodium salt of EDTA | 4.0 |
| Propylene glycol | 5.0 |

[1]Sodium salt of reaction product of lactic and stearic acid (Patco Products, Kansas City, Missouri)
[2]Methyl hydroxybenzoate
[3]Propyl hydroxybenzoate

EXAMPLE IX

A lotion suitable as a skin lotion is prepared by (1) heating Part A (below) to 72° C., (2) Part B (below) to 75° C. (3) adding Part B to Part A within agitation and (4) adjusting the pH to 5.3 with dilute sodium hydroxide.

| | % Weight |
| --- | --- |
| Part A | |
| Cetyl alcohol | 1.9 |
| Stearyl alcohol | 3.0 |
| Isopropyl myristate | 1.3 |
| Light silicone oil | 0.8 |
| "Emplex" | 1.1 |
| Methyl paraben | 0.15 |
| Propyl paraben | 0.05 |
| Part B | |
| Deionized water | 81.7 |
| Propylene glycol | 3.0 |
| Disodium salt of EDTA | 7.0 |

EXAMPLE X

The compositions described in Examples VIII and IX may be applied to dermal surfaces to reduce formation of fatty acids by the action of Corynebacterium species on exuded sebum, said fatty acids being undesirable in inflammatory skin disorders.

EXAMPLE XI

A hand and body lotion suitable for malodor control is prepared by (1) heating Part A (below) to 82° C., (2) heating Part B (below) to 78° C., (3) adding Part A to Part B with stirring and (4) cooling to 46° C. and adding Part C.

|  | % Weight |
|---|---|
| Part A |  |
| Mineral Oil | 3.00 |
| Glyceryl monostearate | 5.00 |
| Isopropyl palmitate | 3.00 |
| Amerchol-H-9[1] | 1.00 |
| Stearic acid | 1.50 |
| Propyl paraben | 0.05 |
| Part B |  |
| Methyl paraben | 0.15 |
| Onyxide 500[2] | 0.20 |
| Propylene glycol - USP | 4.00 |
| Glycerine 96% - USP | 3.00 |
| Standapol SHC-301[3] | 2.50 |
| Disodium salt of EDTA | 5.00 |
| Deionized water | 71.35 |
| Part C |  |
| Fragrance | 0.25 |

[1] Sterolatum (Amerchol Products, Inc.)
[2] 2-Bromo-2-nitropropane-1,3-diol (Onyx Co.)
[3] Sulfosuccinate half ester (Henkel Co.)

EXAMPLE XII

A body powder suitable for topical application is prepared by thoroughly mixing the following:

| Trisodium ethylenediaminetetraacetate | 10 g. |
|---|---|
| Talc | 787 g. |
| Fragrance | 3 g. |

EXAMPLE XIII

The composition described in Example XII may be applied to dermal surfaces to inhibit formation of malodorous fatty acids by the action of Corynebacterium species on exuded sebum.

EXAMPLE XIV

A sanitary napkin is prepared having an absorbent core of comminuted wood pulp and a nonwoven porous cover, and having on the upper surface of the wood pulp core sodium nitrilotriacetate in an amount of 1.0 milligram per square inch of surface area. In its preparation, the nitrilotriacetate is applied to the absorbent core in dry state from an aerosol spray employing dichlorodifluoromethane as a propellant after which the nonwoven cover is placed around the core.

EXAMPLE XV

A sanitary napkin similar to that described in Example XIV except that both the upper surface of the wood pulp core and the fluid pervious cover has applied thereto sodium N-hydroxyethylethylenediaminetriacetate (HEDTA salt) at a rate of 1.6 mg. per square inch of surface area.

EXAMPLE XVI

A catamenial tampon is prepared having an absorbent compressed, cylindrical core of tissue pulp and short rayon fibers. The leading one-half of the surface of the core has applied thereto 1.5 mg. per square inch of a neutral blend of di- and tetrasodium ethylenediaminetetraacetate. The salt is applied to the core surface in a dry state from an aerosol spray employing dichlorodifluoromethane propellant. A nonwoven cover is wrapped around the core and a withdrawal string is knotted around the core at its trailing end.

EXAMPLE XVII

A catamenial tampon similar to that described in Example XVI but wherein the leading two-thirds surface of both the absorbent core and fluid pervious cover have applied thereto 1.0 mg. per square inch of trisodium ethylenediamine tetraacetate.

EXAMPLE XVIII

A cream stick was prepared by admixing at about 60° C. the following materials in the indicated proportions:

| Component | Weight in Grams |
|---|---|
| Ozokerite wax | 48.0 |
| Carnauba wax | 32.0 |
| Candellila wax | 64.0 |
| Emcol 249-3K[1] | 42.0 |
| Tenox 4[2] | 0.8 |
| Benton M-20[3] | 80.0 |
| Talc | 120.0 |
| Propyl paraben | 0.8 |
| Neutral blend of Na$_2$EDTA plus Na$_4$EDTA[4] | 40.0 |

[1] Alkoxylated alcohol (Witco Chemical Company)
[2] 20% Butylated hydroxy anisole, 20% butylated hydroxy toluene, 60% corn oil (Eastman Chemical Products Inc.)
[3] Modified bentonite (National Lead Company)
[4] Prepared as described in the Footnote 5 to Table III.

Thereafter the mixture was poured into chilled molds to provide a final product in chilled stick form.

Test panelists were provided with two coded cream sticks for axillary deodorant use, one stick being of the above composition and the other stick of similar composition but not containing the blend of the two sodium ethylenediaminetetraacetate salts. The test panelists were not informed as to which stick contained the EDTA salts.

The subjects applied one stick to one axilla and the other stick to the other axilla and after each application the subjects made qualitative evaluations on odor intensity. The results are given in Table VI.

TABLE VI

| Panelist | Odor Intensity by Self-Evaluation | |
|---|---|---|
|  | Control Axilla | Test Axilla |
| A | Strong | No odor |
| B | Very Strong | No Odor |
| C | Very Strong | No Odor |
| D | Strong | No Odor |
| E | Strong | No Odor |
| F | Very Strong | Slight |
| G | Very Strong | Slight |
| H | Strong | Slight |
| I | Very Strong | Slight |
| J | Very Strong | Slight |

TABLE VI-continued

| | Odor Intensity by Self-Evaluation | |
|---|---|---|
| Panelist | Control Axilla | Test Axilla |
| K | Strong | Slight |
| L | Strong | Slight |
| M | Very Strong | Slight |

EXAMPLE XIX

An aerosol composition is prepared by first admixing the following materials in the indicated proportions:

| | Parts by Weight |
|---|---|
| Micropulverized Talc | 2.50 |
| Micropulverized Na₃EDTA | 2.50 |
| Fragrance | 0.16 |
| Anhydrous ethanol | 0.20 |
| Isopropyl myristate | 0.60 |

Thereafter, the mixture is placed in vessels suitable for pressurization (cans) and the following propellants added in the indicated proportions:

| | |
|---|---|
| Freon 11[1] | 47.02 |
| Freon 12[2] | 47.20 |

[1]Trichloromonofluoromethane (E.I. duPont de Nemours & Co.)
[2]Dichlorodifluoromethane (E.I. duPont de Nemours & Co.)

EXAMPLE XX

In an experiment carried out in a manner similar to that described in Example V, test samples were prepared by adding to samples of sterile plasma inoculated with Corynebacterium, one of the following aminopolycarboxylic acid compounds: disodium ethylenediaminetetraacetate (Na₂EDTA), N-hydroxyethylethylenediaminetriacetic acid (HEDTA), diethylenetriaminepentaacetic acid (DTPA), ethylene glycol bis(aminoethyl ether)tetracetic acid (EGTA), and a triethanolamine salt of ethylenediaminetetracetic acid (TEDTA) prepared by adding triethanolamine to aqueous ethylenediaminetetraacetic acid to a pH of 6.3. The amount of aminopolycarboxylic acid compound added to the samples was that sufficient to provide in the test media 0.2% by weight of the aminopolycarboxylic acid compound (calculated as the free acid). In addition two control samples were prepared: One control sample was of unmodified sterile plasma (uninoculated and containing no aminopolycarboxylic acid compound) and the second control sample was an inoculated sample containing no aminopolycarboxylic acid compound and served as untreated control. The samples were incubated and tested for free fatty acids as previously described. The results obtained were as follows:

TABLE VII

| | Fatty Acids Produced (ppm) | |
|---|---|---|
| | Isobutyric | Isovaleric |
| Untreated Sterile Plasma | 0 | 0 |
| Corynebacterium Inoculum No Aminopolycarboxylic Acid Compound | 105 | 187 |
| Corynebacterium Inoculum + 0.1% Na₂EDTA | 0 | 0 |
| Corynebacterium Inoculum + 0.1% HEDTA | 0 | 0 |
| Corynebacterium Inoculum + 0.1% DTPA | 0 | 0 |
| Corynebacterium Inoculum + 0.1% EGTA | 0 | 0 |
| Corynebacterium Inoculum + 0.1% TEDTA | 0 | 0 |

EXAMPLE XXI

Sanitary napkins are prepared having an aminopolycarboxylic acid compound impregnated on the upper surface of the absorbent core and fluid pervious cover in a manner similar to that described in Examples XIV and XV except that they are modified with respect to the aminopolycarboxylic acid compound and amount employed per square inch of surface area as follows:

Disodium ethylene glycol bis(aminoethyl ether)tetracetate, 3 mg. per square inch.

Sodium iminodiacetate, 2 mg. per square inch.

Ethylenediaminetetra(methylenephosphonic acid)-neutralized with diethanolamine to pH 6.3, 1.5 mg. per square inch.

Pentasodium nitrilotris(methylenephosphonate), 2 mg. per square inch.

Ethylenediaminetetra(methylenesulfonic acid) neutralized with triethanolamine to pH 6.3, 2 mg. per square inch.

EXAMPLE XXII

A cream stick is prepared in the manner described in Example XVIII by admixing the following materials in the indicated proportions:

| Component | Weight in Grams |
|---|---|
| Ozokerite wax | 48.0 |
| Carnauba wax | 32.0 |
| Candellila wax | 64.0 |
| Emcol 249-3K | 42.0 |
| Tenox 4 | 0.8 |
| Benton M-20 | 80.0 |
| Talc | 120.0 |
| Propyl paraben | 0.8 |
| Triethanolamine salt of ethylanediaminetetraacetic acid | 50.0 |

The stick may be applied to the dermal surfaces of the axilla to inhibit formation of odorous fatty acids by action of Corynebacterium on lipoidal materials.

EXAMPLE XXIII

Compositions suitable for topical application to inhibit fatty acid production from lipoidal materials by Corynebacterium may be prepared by intimately admixing the components specified below in the amounts indicated to obtain treating compositions:

| | |
|---|---|
| Composition A | |
| N—Hydroxyethylethylene-diaminetetraacetic acid | 10 parts by weight |
| Triethanolamine | 10 parts by weight |
| Witch hazel | 80 parts by weight |
| Composition B | |
| Ethylene glycol bis(aminoethyl-ether)tetraacetic acid | 13 parts by weight |
| Triethanolamine | 13.8 parts by weight |
| Witch hazel | 73.2 parts by weight |

-continued

| Composition C | |
|---|---|
| Ethylenediaminetetraacetic acid | 10 parts by weight |
| Triisopropanolamine | 17.7 parts by weight |
| Witch hazel | 72.3 parts by weight |

EXAMPLE XXIV

A composition suitable for application to dermal tissue is prepared by intimately admixing the following:

| Ethylenediaminetetracetic acid | 10 parts by weight |
|---|---|
| Triethanolamine | 13.8 parts by weight |
| Witch hazel | 76.2 parts by weight |

This composition may be applied to dermal tissues to inhibit development of inflammatory skin conditions resulting from fatty acids arising from secreted lipoidal materials by the action of Corynebacterium thereon. In such use daily application is made by swabbing the affected area of the dermal surface and repeating such application until the condition is alleviated. Further application may be made on the appearance of development of the undesirable conditions to prevent further development of said conditions.

EXAMPLE XXV

The composition of Example XXIV was employed to determine efficacy in inhibiting undesirable inflammatory conditions of the skin typical of acne. The undesirable conditions may be those described as the existence of erythema and the presence of papules and pustules.

In the determination, six subjects with similar degree of inflammatory conditions on both sides of the face applied the above composition to one side of the face after first making determinations on the number of erythemous papules and pustules on each side of the face, herein termed "lesions." The other side of the face served as control. The applications were made twice daily to one side of the face after first separately cleaning each side of the face, and the application was continued for a period of three weeks. At the end of this period the percent change in the number of lesions on the treated and untreated sides of the face were determined. The results were as follows:

TABLE VII

| Panelist | Percent Change | |
|---|---|---|
| | Treated | Untreated |
| 1 | 70% Reduction | 6% Reduction |
| 2 | 70% Reduction | 55% Increase |
| 3 | 52% Reduction | 7% Increase |
| 4 | 62% Reduction | 20% Increase |
| 5 | 62% Reduction | 3% Reduction |
| 6 | 59% Reduction | 5% Reduction |

Although in the past, undesirable products resulting from microbial action on body secretions have been inhibited by kill of microorganisms, it has now been discovered that by use of the compositions of the present invention, the desired inhibitory action may be accomplished without the necessity of kill of the organisms. Thus, for example, when growth of Proteus mirabilis in heparinized blood at 37° with and without added disodium ethylenediaminetetraacetate was followed over a 24-hour period, there was found to be no detrimental effect on the growth of organisms as can be seen in the following table:

| Blood Inoculated With Proteus Mirabilis | Bacterial Count | |
|---|---|---|
| | 0 Hours | 24 Hours |
| No Na$_2$EDTA | $100 \times 10^4$ | $182 \times 10^7$ |
| 2% Na$_2$EDTA | $100 \times 10^4$ | $231 \times 10^7$ |

What is claimed is:

1. A method of inhibiting the formation of fatty acids having from 4 to 18 carbon atoms per molecule from the degradation of skin secretions by Corynebacterium comprising applying to the skin, in an amount effective to inhibit the formation of said fatty acids, a composition comprising a carrier suitable for topical application and, as the sole essential ingredient, an aminopolycarboxylic compound selected from the group consisting of ethylenediaminetetraacetic acid, diethylenetriaminepentaacetic acid, N-hydroxyethylethylenediaminetriaacetic acid, triethylenetetraaminehexaacetic acid, 1,2-diaminocyclohexane-N,N'-tetraacetic acid, N,N-dihydroxyethylethylenediaminediacetic acid, iminodiacetic acid, hydroxyethyliminodiacetic acid, nitrilotriacetic acid and their water soluble salts; said aminopolycarboxylic compound being present in a concentration of 0.5 to 10 weight percent in said composition, based on the weight of the free acid, said composition maintaining the viability of said Corynebacterium.

2. A method of inhibiting the formation of fatty acids having from 4 to 18 carbon atoms per molecule from the degradation of skin secretions by Corynebacterium comprising applying to the skin, in an amount effective to inhibit the formation of said fatty acids, a composition comprising a carrier suitable for topical application and, as the sole essential ingredient, a water-soluble salt of ethylenediaminetetraacetic acid in a concentration of 0.5 to 10 weight percent of said acid in said composition based on the weight of the free acid, said composition maintaining the viability of said Corynebacterium.

3. The method of claim 2 wherein said water-soluble salt is an alkali metal salt.

4. The method of claim 3 wherein said water-soluble salt is a sodium salt.

5. The method of claim 4 wherein said water-soluble salt is disodium-ethylenediaminetetraacetic acid.

6. The method of claim 4 wherein said water-soluble salt is trisodium-ethylenediaminetetraacetic acid.

7. The method of claim 4 wherein said water-soluble salt is tetrasodium-ethylenediaminetetraacetic acid.

8. The method of claim 4 wherein said water-soluble salt is a mixture of disodium and tetrasodium-ethylenediaminetetraacetic acid.

9. The method of claim 2 wherein said water-soluble salt is a lower alkanolamine salt.

10. The method of claim 2 wherein said water-soluble salt is the trialkanolamine salt of ethylenediaminetetraacetic acid.

11. A method of inhibiting the formation of lower fatty acids from the degradation of skin secretions in the axillary area by Corynebacterium comprising applying to the skin in the axillary area, in an amount effective to inhibit the formation of said fatty acids, a composition comprising a carrier suitable for topical application and, as the sole essential ingredient, a water-soluble salt of ethylenediaminetetraacetic acid in a concentration of 0.5 to 10 weight percent of said acid in said composition based on the weight of the free acid, said composition maintaining the viability of said Corynebacterium.

12. The method of claim 11 wherein said lower fatty acids comprise fatty acids having no more than five carbon atoms.

13. The method of claim 12 wherein said water-soluble salt is an alkali metal salt.

14. The method of claim 13 wherein said water-soluble said is a sodium salt.

15. The method of claim 14 wherein said water-soluble salt is disodium-ethylenediaminetetraacetic acid.

16. The method of claim 14 wherein said water-soluble salt is trisodium-ethylenediaminetetraacetic acid.

17. The method of claim 14 wherein said water-soluble salt is tetrasodium-ethylenediaminetetraacetic acid.

18. The method of claim 14 wherein said water-soluble salt is a mixture of disodium and tetrasodium-ethylenediaminetetraacetic acid.

19. The method of claim 12 wherein said water-soluble salt is a lower alkanolamine salt.

20. The method of claim 12 wherein said water-soluble salt is the trialkanolamine salt of ethylenediaminetetraacetic acid.

21. A method of treating inflammatory skin conditions comprising inhibiting the formation of fatty acids of up to about 18 carbon atoms from the degradation of skin secretions by Corynebacterium comprising applying to the skin in an amount effective to inhibit the formation of said fatty acids, a composition comprising a carrier suitable for topical application and, as the sole essential ingredient, a water-soluble salt of ethylenediaminetetraacetic acid in a concentration of from 2 to 15% by weight of said acid in said composition, based on the weight of the free acid, said composition maintaining the viability of said Corynebacterium.

22. The method of claim 21 wherein said water-soluble salt is an alkali metal salt.

23. The method of claim 22 wherein said water-soluble salt is a sodium salt.

24. The method of claim 23 wherein said water-soluble salt is disodium-ethylenediaminetetraacetic acid.

25. The method of claim 23 wherein said water-soluble salt is trisodium-ethylenediaminetetraacetic acid.

26. The method of claim 23 wherein said water-soluble salt is tetrasodium-ethylenediaminetetraacetic acid.

27. The method of claim 23 wherein said water-soluble salt is a mixture of disodium and tetrasodium-ethylenediaminetetraacetic acid.

28. The method of claim 21 wherein said water-soluble salt is a lower alkanolamine salt.

29. The method of claim 21 wherein said water-solusble salt is the trialkanolamine salt of ethylenediaminetetraacetic acid.

* * * * *

UNITED STATES PATENT AND TRADEMARK OFFICE
CERTIFICATE OF CORRECTION

PATENT NO. : 4,356,190
DATED : October 26, 1982
INVENTOR(S) : Kenneth S. Kraskin It is certified that error appears in the above-identified patent and that said Letters Patent is hereby corrected as shown below:

In Claim 14, line 2, delete "said" and substitute therefor -- salt -- after the word "water-soluble".

Signed and Sealed this

Fifteenth Day of February 1983

[SEAL]

Attest:

Attesting Officer

GERALD J. MOSSINGHOFF
Commissioner of Patents and Trademarks